United States Patent [19]

Vallée et al.

[11] Patent Number: 6,008,267
[45] Date of Patent: Dec. 28, 1999

[54] POLYIONIC POLYMERIC COMPOUNDS, PROCESS OF PREPARING SAME AND USE THEREOF AS PHOTOINITIATORS

[75] Inventors: Alain Vallée, Varennes; Michel Armand, Montréal, both of Canada; Xavier Ollivrin; Christophe Michot, both of Grenoble, France

[73] Assignees: Hydro-Québec, Montréal, Canada; Centre National de la Recherche Scientifique, Paris, France

[21] Appl. No.: 08/943,590

[22] Filed: Oct. 3, 1997

[30] Foreign Application Priority Data

Oct. 3, 1996 [CA] Canada ................. 2187046

[51] Int. Cl.⁶ ........................... C08F 2/46
[52] U.S. Cl. ............................. 522/31
[58] Field of Search ................ 522/31

[56] References Cited

U.S. PATENT DOCUMENTS

| | | |
|---|---|---|
| 3,632,843 | 1/1972 | Allen et al. |
| 4,031,036 | 6/1977 | Koshar. |
| 5,527,655 | 6/1996 | Bonham et al. ............... 430/175 |
| 5,534,623 | 7/1996 | Wade et al. .................... 534/560 |
| 5,550,171 | 8/1996 | Kuczynski ..................... 522/31 |
| 5,554,664 | 9/1996 | Lamanna et al. .............. 522/25 |

*Primary Examiner*—Nathan M. Nutter
*Attorney, Agent, or Firm*—Oblon, Spivak, McClelland, Maier & Neustadt, P.C.

[57] ABSTRACT

Polymer or oligomer ionic compound made of a polycationic part $(A^+)_p$ comprising a plurality of onium units and a sufficient number of anions $X^-$ to provide electrical neutrality to the compound, characterized in that the onium units are selected from the group consisting of biaryliodonium, arylsulfonium, arylacylsulfonium, diazonium, organometallic cations comprising a transition metal which is complexed by at least one unsaturated cycle comprising 4 to 12 carbon atoms;

$X^-$ is an imide anion $[R_F SO_2 NSO_2 R'_F]^-$ or a methylide anion $[R_F SO_2 C(Q) SO_2 R'_F]^-$ in which:

1) Q represents:
   H—, Cl—, F—, Br— or CN—;
   an alkyl radical having 1 to 30 carbon atoms;
   an aryl, alkylaryl or arylakyl radical having 6 to 30 carbon atoms;
   a group $R''_F$ or a group $R''_F SO_2$;

2) $R_F$ and $R'_F$, as well as $R''_F$ possibly when $X^-$ is a methylide anion, are independently selected from the group consisting of fluorine, perhaloalkyl groups having 1 to 30 carbon atoms, (perhaloalkyl)alkyloxy groups, perhalogenated cycloaliphatic groups having 3 to 30 carbon atoms possibly containing hetero atoms selected from O and N, and/or possibly comprising at least one perhaloalkyl chain, the perhalogenated aryl having 6 to 30 carbon atoms; or 3) $R_F$ and $R'_F$ together form a bivalent radical constituting a cycle respectively with group —$SO_2$—N—$SO_2$— or with group —$SO_2$—C(Q)—$SO_2$—, or when $X^-$ is a methylide anion, $R''_F$ constitutes with one of the radicals $R_F$ or $R'_F$ a bivalent radical constituting a cycle respectively with group —$SO_2$—C—$SO_2$— or group —$SO_2$—C—, said bivalent radical being selected from perfluorinated alkylene radicals having 2 to 12 carbon atoms, the third radical which is possibly present being selected from the monovalent radicals mentioned above in 2);

4) p represents the number of onium units.

These compounds are useful as photoinitiators for cationic polymerization or cross-linking of monomers or for the modification of polymers for example when they are used as photoresists. The preparation of these compounds is also disclosed.

32 Claims, No Drawings

POLYIONIC POLYMERIC COMPOUNDS, PROCESS OF PREPARING SAME AND USE THEREOF AS PHOTOINITIATORS

BACKGROUND OF INVENTION a) Field of the Invention

The present invention concerns polyionic compounds, the process of preparation and use thereof as photoinitiators for the cationic polymerization or cross-linking of monomers and prepolymers, or for the modification of the solubility parameters of certain polymers which can be used as photoresists.

b) Description of Prior Art

A polymerization which involves a mechanism of the cationic type has many advantages. In particular, it is fast, even at low temperature, the coefficient of utilization of the monomer is high and the sensitivity towards atmospheric contaminants, such as oxygen, is low as compared to radical or anionic polymerizations.

Monomers, prepolymers and polymers containing cycloaliphatic epoxy functions, and vinyl ethers are increasingly used, for example in the paint, varnish, ink, glue, and antiadhesive support industries. Moreover, vinyl ethers generally appear to be non-toxic as opposed to acrylates and methacrylates. Monomers and prepolymers of the epoxy or vinyl ether types may be polymerized according to various methods, ionic polymerization being particularly preferred.

Cationic polymerization catalysts are generally considered as being acids within the meaning of Bronsted HX (proton donors) or as being acids within the meaning of Lewis (acceptors of electronic doublets), the latter operating in the presence of a co-catalyst which is a source of protons. These acids may be sufficiently strong to ensure the stability of the cationic species which is carried either by the monomer or by the growing macromolecular chain, which means that the corresponding anion $X^-$ should have a nucleophilic power which is as low as possible. The Bronsted acids which are most commonly used as cationic polymerization catalysts are $CF_3SO_3H$, $HClO_4$, $HBF_4$, $HPF_6$, $HAsF_6$ and $HSbF_6$. These acids are classified as follows with respect to speeds of initiation of propagation as well as of obtention of the highest molecular weights:

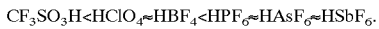

$CF_3SO_3H < HClO_4 \approx HBF_4 < HPF_6 \approx HAsF_6 \approx HSbF_6$.

More recently compounds with an acid character have also been used, such as bis(perfluoroalkylsulfonyl)imide (U.S. Pat. No. 4,031,036 Koshar et al.) or bis (perfluoroalkylsulfonyl)methane (U.S. Pat. No. 3,632,843 Allen et al).

It is known that the in situ preparation of polymerization catalysts has many advantages. The in situ production of an acid which is capable of catalyzing the cross-linking of a monomer enables indeed to obtain a monomer or a fluid prepolymer (thermoplastic material or solution) and to give it its final properties, for example by the simple action of a radiation. This technique is very much in use for inks, paints, adhesive films and anti-adhesive films. It should also be noted that the in situ preparation of the acid from a salt, in many cases enables to dispense with the stocking and handling of acid compounds which are more corrosive than the corresponding salts.

The catalysts may be prepared in situ by heat treatment. For example, ammonium or metal salts of bis (perfluoroalkylsulfonyl)imide (U.S. Pat. No. 4,031,036 Koshar et al.) or ammonium or amine salts of bis (perfluoroalkylsulfonyl)methane (U.S. Pat. No. 3,632,843 Allen et al.) have been used to obtain in situ, by heating, bis(perfluoroalkylsulfonyl)imide or the corresponding bis (perfluoroalkylsulfonyl)methane which thereafter act as catalysts. These catalysts called "latent", present, however, only a limited interest because of the necessity of extended heating at high temperature to achieve the removal of the acid, this removal being in addition progressive and not integral at the start. The result is that, on the one hand, the reaction speed is slow and, on the other hand, the polymers obtained are of poor quality with respect to molecular mass, polydispersity and coloring.

Acid catalysts may also be prepared in situ by actinic radiation (such as photons in which the wavelength corresponds to ultraviolet, visible, γ and X radiation), or with β-radiation (beam of electrons) on a suitable salt. Such salt, which is chemically labile under the action of an actinic or β-radiation which reduces the release of the corresponding acid having a strong catalytic activity, is a photoinitiator. The advantages of such a process are numerous: the release of the catalyst by radiation is rapid and practically complete which results in a simultaneous initiation of the growth of the chains and therefore a more homogeneous distribution of the masses with less polydispersity and better mechanical properties. Polymerization may be carried out at a relatively low temperature which prevents the decomposition or coloring of the materials obtained, as well as the formation of bubbles when a solvent is used or when the reaction mixture contains a volative additive which is designed to be maintained in the final material and which plays the role of plasticizing agent.

The capacity of different salts (hexafluoroantimonates, hexafluoroarseniates, hexafluoroplatinates and tetrafluoroborates) of aryldiazonium, aryliodonium, arylsulfonium, arylacylsulfonium or areneferrocenium to form acids (respectively $HSbF_6$, $HAsF_6$, $HPF_6$, $HBF_4$), under the action of actinic radiation, which can be used as cationic polymerization catalysts, is known. However, all these salts have a toxicity which is not negligible and which is mainly associated with the central element of the anion part, Sb, As, P and B, as well as with the fluorine ions which may be released during the reaction of photolysis or during a later treatment of the polymer (fusion, extrusion . . . ). To fix a general value, diphenyl-iodonium hexafluoroantimonate has an LD50 of 40 mg/kg (measured according to Test No. 10929 TAR) and falls in the category of products classified as "highly toxic".

Other salts containing cations of the same nature but containing less toxic anions have then been proposed. Thus, U.S. Pat. No. 5,554,664 describes salts in which the anion is selected from tris(alkylsulfonyl)methylides, tris (arylsulfonyl)-methylides, bis(alkylsulfonyl)imides and bis (arylsulfonyl)imides in which the alkyl group or the aryl group is perfluorinated or is highly fluorinated and whose cation is an iodoniun, a sulfonium or an organometallic. These compounds may be used, for example, as polymerization initiators after activation in situ. When these salts are used as polymerization photoinitiators, they leave, after decomposition initiated by actinic radiation, fragments which may diffuse at the surface of the material and modify the chemical properties, adhesiveness or appearance in a very notable manner. In the case of sulfonium salts, these residues contain thiols and thioethers in which the repulsive odor is perceptible at extremely low rates, which limits the use of these salts to particular applications. These compounds are also corrosive towards metals, such as copper or various components used in microelectronics. Thus, Kukzynski (U.S. Pat. No. 5,550,171) considers that the diffusion of the catalytic residues is the main cause of failure of computer storage discs.

Photosensitive polymers produced by the association of a polydiazonium polycation and a polysulfonate polyanion are described in U.S. Pat. No. 5,527,655. Such polymers are used to increase cross-linking efficiency. The solubility of these complexes is only obtained with diazodium contents clearly lower than 10% by weight and only in the presence of quartenary ammonium salts which are used for decreasing electrostatic interactions. U.S. Pat. No. 5,534,623 describes a composition based on polydiazoniun associated with contra-ions of the type $PF_6$ intended for the preparation of photoresists. These anions are, however, toxic and are not compatible with microelectronics because they contain an element which is capable of contaminating silicon (B, P, As or Sb).

It is also known to use acids produced by means of actinic radiation in order to degrade the resins contained in a film constituting a photoresist. This technique is particularly efficient for photoresists with chemical amplification in which very small quantities of protons catalyze the decomposition of groups, such as esters containing a group derived from a tertiary alcohol (such as for example a tertiobutyl group) which is part of a macromolecular chain. This technique thus enables to modify the solubility parameters of the resin exposed to actinic radiation and to carry out masking and selective engraving operations such as those used in microelectronics.

When a photoresist composition or a resin composition with chemical amplification used in microlithography contains a photoinitiator, it is considered that the diffusion of the ionic species of the initiator or of the acid formed determines the limit of spatial resolution which is many tens of microns with non-polymer initiators. Now, actually resolutions lower than 1 micron are requested for the electronic industry of microprocessors and memories.

SUMMARY OF INVENTION

The inventors have now found ionic compounds which, under the action of an actinic or β-radiation, enable to obtain acids which reveal themselves as good catalysts for cationic polymerization or for modification of polymers. Contrary to what is expected from the behavior which is inherent to polyelectrolytes, i.e., a solubility which is limited to solvents with very high polarity, these materials are soluble or dispersible in the usual organic solvents or monomers intended to be polymerized or mixtures thereof.

It is therefore an object of the present invention to provide a new family of compounds, a process for their preparation as well as their use as photoinitiators for the cationic polymerization or cross-linking of monomers or for the modification of polymers, for example when they are used as photoresists.

A compound of the present invention is an oligomer or a polymer ionic compound consisting of a polycationic part $AP^+$ comprising a plurality of onium units and a number of anions $X^-$ which are sufficient to ensure electrical neutrality of a compound and is characterized in that:

the onium units are selected from the group consisting of biaryliodonium, arylsulfonium, arylacylsulfonium, and diazonium compounds, and organometallic cations comprising a transition metal which is complexed with at least one unsaturated cycle comprising 4 to 12 carbon atoms;

$X^-$ is an imide anion $[R_FSO_2NSO_2R'_F]^-$ or a methylide anion $[R_FSO_2C(Q)SO_2R'_F]^-$ in which 1) Q represents
H—, Cl—, F—, Br—or CN—;
an alkyl radical having 1 to 30 carbon atoms;
an aryl, alkylaryl or arylalkyl radical having 6 to 30 carbon atoms;
a group $R''_F$ or a group $R''_FSO_2$;

2) $R_F$ and $R'_F$ as well as $R''_F$, possibly when $X^-$ is a methylide anion, are independently selected from the group consisting of fluorine, perhaloalkyl groups having 1 to 30 carbon atoms, (perhaloalkyl)alkoxy groups, perhalogenated cycloaliphatic groups having 3 to 30 carbon atoms which may contain heteroatoms selected from O and N, possibly carrying at least one perhaloalkyl chain, and perhalogenated aryl groups having 6 to 30 carbon atoms; or 3) $R_F$ and $R'_F$ together form a bivalent radical constituting a cycle respectively with the group —$SO_2$—N—$SO_2$ or with the group —$SO_2$—C(Q)—$SO_2$ or when $X^-$ is a methylide anion, $R''_F$ forms with one of the radicals $R_F$ or $R'_F$ a bivalent radical constituting a cycle respectively with the group —$SO_2$—C—$SO_2$ or with the group —$SO_2$—C—, said bivalent radical being selected from perfluorinated alkylenes having 2 to 12 carbon atoms, the third radical which may possibly be present being selected from the monovalent radicals mentioned above in 2);

4) p represents the number of onium units and consequently the number of associated anions $X^-$.

As particularly interesting examples of $X^-$, sulfonimides anions $[R_FSO_2NSO_2R'_F]^-$ in which $R_F$ and $R'_F$ are independently selected from the group consisting of perfluoroalkyl groups having 1 to 10 carbon atoms (preferably $CF_3$—, $C_2F_5$—, $C_4F_9$—, $C_6F_{13}$—, $C_8F_{17}$— and $C_{10}F_{21}$), or those in which $R_F$ and $R'_F$ together form a linear perfluoroalkylene bivalent radical having 1 to 8 carbon atoms may be mentioned.

Other anions may also be mentioned including the sulfonylmethylides anions $[R_FSO_2C(Q)SO_2R'_F]^-$ in which Q is selected from the group consisting of alkyl, aryl, alkylaryl or arylalkyl groups having at most 30 carbon atoms, perfluoroalkylsulfonyl groups having 1 to 8 carbon atoms (preferably $CF_3SO_2$—, $C_2F_5SO_2$—, $C_4F_9SO_2$—, $C_6F_{13}SO_2$— and $C_8F_{17}SO_2$—) and perfluoroalkyl radicals having 1 to 12 carbon atoms (preferably $CF_3$—, $C_2F_5$—, $C_4F_9$—, $C_6F_{13}$—, $C_8F_{17}$— and $C_{10}F_{21}$—), and $R_F$ and $R'_F$ are independently selected from the group consisting of alkyl radicals having 1 to 10 carbon atoms (preferably $CF_3$—, $C_2F_5$—, $C_4F_9$—, $C_6F_{13}$—, $C_8F_{17}$— and $C_{10}F_{21}$—), or $R_F$ and $R'_F$ together form a linear perfluoroalkylene bivalent radical having 1 to 8 carbon atoms.

The anions $[R_FSO_2NSO_2R'_F]^-$ and $R_FSO_2C(SO_2R''_F)SO_2R'_F]^-$ in which $R_F$ and $R'_F$ and $R''_F$ each represent a perfluoroalkyl group having 1 to 10 carbon atoms, preferably 1 to 6 carbon atoms, are particularly advantageous, as well as the compounds $[R_FCH_2—O—SO_2)_2N]^-$ and $[(R_F)_2CH—0—SO_2)_2N]^-$.

A particular family of compounds according to the invention comprises polyiodonium salts which correspond to one of the following Formulae (I), (II), (III) or (IV):

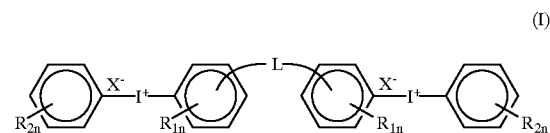

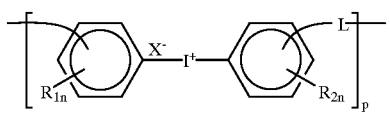

(II)

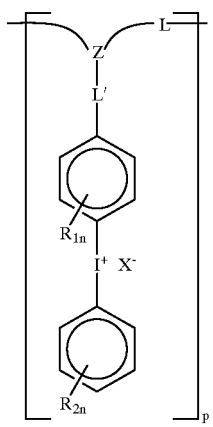

(III)

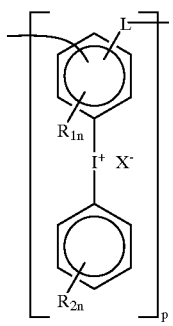

(IV)

in which:
- a1) $R_{1n}$ represents 1 to 4, preferably 1 to 2 groups which are identical or different and are bound to any free carbon atoms of the aryl group, $R_{2n}$ represents 1 to 4, preferably 1 to 2 groups which are identical or different and are bound to any free carbon atoms of the aryl group, groups $R_{1n}$ and $R_{2n}$ being independently selected from one another among:
  - linear or branched alkyl or arylalkyl radicals having 1 to 30 carbon atoms;
  - alkenyl radicals having 1 to 30 carbon atoms;
  - aryl or alkylaryl radicals having 6 to 30 carbon atoms including those which have condensed nuclei;
  - radicals having 1 to 30 carbon atoms and selected from the group consisting of oxaalkyls, azaalkyls, thiaalkyls, phosphaalkyls, oxaalkylenes, azaalkylenes, thiaalkylenes, phosphaalkylenes;
  - radicals having 1 to 30 carbon atoms and including a sulfoxide group, a sulfone group, a phosphine oxide group, a phosphonate group, all these radicals being obtained by the addition of oxygen on sulfur or phosphorus atoms;
  - aromatic or alicyclic heterocyclic radicals comprising at least one heteroatom selected from the group consisting of O, N, S and P;
  - or two substituents selected from $R_{1n}$ and $R_{2n}$ which together form a bivalent radical which constitutes a cycle with the group which carries them, said bivalent radical being selected from the group consisting of linear alkylene radicals having 1 to 18 carbon atoms, benzo biradicals which may have at least one substituent preferably selected from the group consisting of alkyl, oxaalkyl or alkenyl radicals having 1 to 10 carbon atoms, oxaalkylene groups having the formula —R'—(OCH$_2$CH$_2$)$_q$—O—R'— or —R'—[OCH(CH$_3$)CH$_2$]$_q$—O—R'— in which R' is a linear alkylene radical having 0 to 18 carbon atoms and $1 \leq q \leq 22$;

- a2) L' represents a bivalent radical selected from the group consisting of linear alkylene radicals having 1 to 18 carbon atoms, phenylene groups which are substituted or non-substituted, oxaalkylene groups having the formula —R'—(OCH$_2$CH$_2$)$_q$—O—R'— or —R'—[OCH(CH$_3$)CH$_2$]$_q$—O—R'— in which R' is a linear alkylene radical having 0 to 18 carbon atoms and $1 \leq q \leq 22$, —O—, —S—, >C=O, siloxane groups —R'—O—[Si(R)$_2$O]$_r$—R' or —O—[Si(R)$_2$O]$_{5r}$— $1 \leq r \leq 40$ in which R' has the meaning given above and R is selected from the group consisting of linear alkyl radicals having 1 to 18 carbon atoms, 2-ethylhexyl, phenyl (preferably R is CH$_3$ or phenyl), or a direct bond between two carbon atoms of two non-condensed aryl groups;

- a3) L represents a bivalent radical selected from the group defined in point a2) above for L'; or L represents a segment consisting of at least one monomer unit which is non-ionic or possesses an ionic group which is not sensitive towards the action of actinic radiation (in this case L representing the average space between the active ionic groups);

- a4) p represents the number of recurring units, $2 \leq p \leq 1000$;

- a5) Z represents —CH, —CR, —N, —SiR, —SiRO$_3$, R being selected from linear alkyl radicals having 1 to 18 carbon atoms, 2-ethylhexyl and phenyl;

- a6) X is as defined previously.

Among the compounds of polyiodonium type, those in which the substituents $R_{1n}$ and $R_{2n}$ are independently selected from the group consisting of linear alkyl radicals having 1 to 18 carbon atoms, 2-ethylhexyl, phenyl, oxaalkyls having the formula R-(OCH$_2$CH$_2$)$_y$— or R-[OCH(CH$_3$)CH$_2$]$_y$— in which R is a linear alkyl radical having 1 to 18 carbon atoms and $1 \leq y \leq 22$, are particularly preferred.

When the polyiodonium compound of the invention has one of the formulae (I) or (II), it is in the form of a dimer or a polymer comprising iodonium ionic groups in the polymer chain.

When the polyiodonium compound has one of the formulae (III) or (IV), it is in the form of a polymer in which the iodonium ionic groups are carried by hanging substituents.

Another specific family of compounds according to the invention comprises polysulfonium salts which are represented by one of the following formulae:

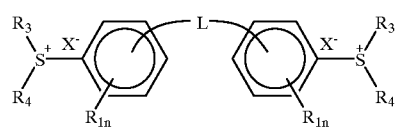

(V)

-continued

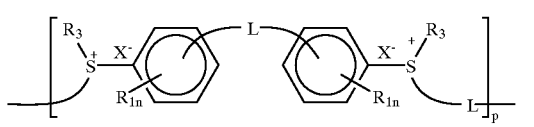
(VII)

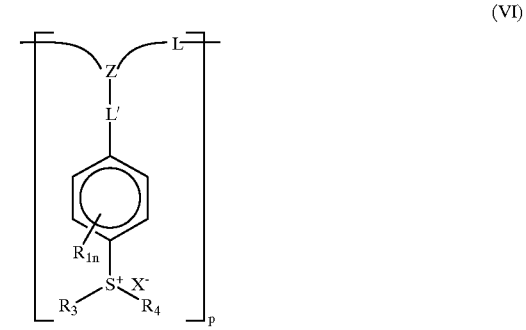
(VI)

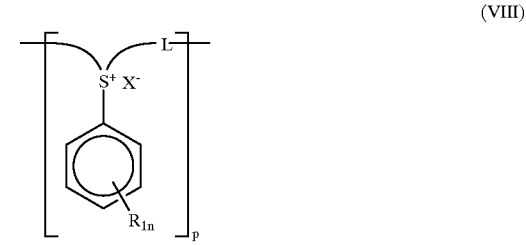
(VIII)

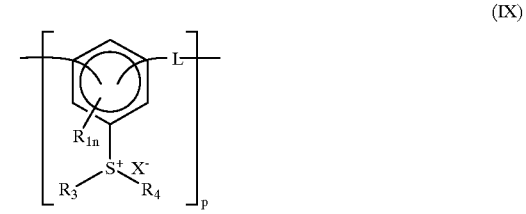
(IX)

in which:
b1) $R_{1n}$ represents 1 to 4, preferably 1 to 2 groups which are identical or different and are bound to any one of the free carbon atoms of the aryl group, the substituents $R_{1n}$ and the substituents $R_3$ and $R_4$ being independently selected from:
   linear or branched alkyl or aryl radicals having 1 to 30 carbon atoms;
   alkenyl radicals having 1 to 30 carbon atoms;
   aryl or alkylaryl radicals having 6 to 30 carbon atoms including those which have condensed nuclei;
   radicals having 1 to 30 carbon atoms and selected from the group consisting of oxaalkyls, azaalkyls, thiaalkyls, phosphaalkyls, oxaalkylenes, azaalkylenes, thiaalkylenes, phophaalkylenes;
   radicals having 1 to 30 carbon atoms including a sulfoxide group, sulfone group, phosphine oxide group, phosphonate group, all these radicals being obtained by addition of oxygen on the atoms of sulfur or phosphorus;
   aromatic or alicyclic heterocyclic radicals comprising at least one heteroatom selected from the group consisting of O, N, S and P;

—NO, —CN, —OH, —Cl, —Br, —I, —F;
or groups $R_3$ and $R_4$ carried by a same sulfur atom on the one hand and/or two substituents selected from $R_{1n}$ on the other hand together forming a bivalent radical which constitutes a cycle with the group which carries them, said bivalent radical being selected from the group consisting of linear alkylene radicals having 1 to 18 carbon atoms, benzo biradicals possibly carrying at least one substituent preferably selected from the group consisting of alkyl, oxaalkyl or alkenyl radicals having 1 to 10 carbon atoms, oxaalkylene groups having the formula —R'—(OCH$_2$CH$_2$)$_q$—O—R'— or —R'—[OCH(CH$_3$)CH$_2$]$_q$—O—R'— in which R' is a linear alkylene radical having 0 to 18 carbon atoms and $1 \leq q \leq 22$;

b2) L' has the meaning given in paragraph a2) above;
b3) L has the meaning given in paragraph a3) above;
b4) p represents the number of recurring units, $2 \leq p \leq 1000$;
b5) Z has the meaning given in paragraph a5) above;
b6) X is as defined previously.

Polysulfonium compounds in which the substituents $R_{1n}$, $R_3$ and $R_4$ are selected from the group consisting of linear alkyl radicals having 1 to 18 carbon atoms, 2-ethylhexyl, phenyl, oxaalkyls, represented by the formula R—(OCH$_2$CH$_2$)$_y$— or R—[OCH(CH$_3$)CH$_2$]$_y$— in which R is a linear alkyl radical having 1 to 18 carbon atoms and $1 \leq y \leq 22$, are particularly preferred.

When a polysulfonium compound of the invention corresponds to Formula (V) it is a dimer. A polysulfonium compound represented by one of the Formulae (VII) or (VIII) is in the form of a polymer carrying ionic groups in the main chain.

When a polysulfonium compound is represented by one of Formula (VI) or (IX), it is in the form of a polymer in which the ionic groups are carried by lateral groups.

Another particular family of compounds according to the invention comprises polyacylsulfonium salts which are represented by one of the following Formulae (X), (XI), (XII), (XIII) or (XIV):

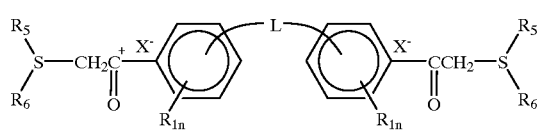
(X)

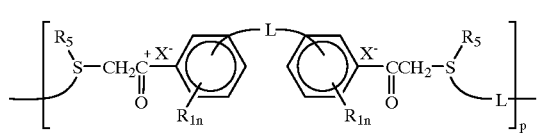
(XII)

-continued

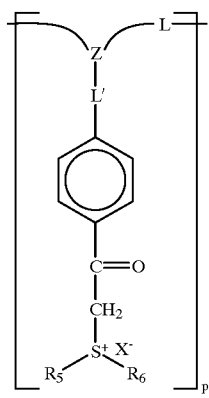
(XI)

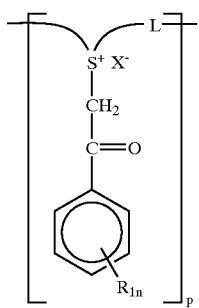
(XIII)

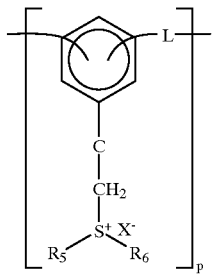
(XIV)

in which c1) $R_{1n}$ has the meaning given above in paragraph b1), and the substituents $R_5$ and $R_6$ have the same meaning as substituents $R_3$ and $R_4$ defined above in paragraph b1);

c2) L' has the same meaning as in paragraph a2) above;

c3) L has the meaning given in paragraph a3) above;

c4) Z has the meaning given above in paragraph a5);

c5) p represents a number of recurring units, $2 \leq p \leq 1000$;

c6) X is as defined previously.

Among the polyacylsulfonium compounds, those in which the substituents $R_{1n}$, $R_5$ and $R_6$ are selected from the group consisting of linear alkyl radicals having 1 to 18 carbon atoms, 2-ethylhexyl, phenyl, oxaalkyls represented by the formula R—$(OCH_2CH_2)_y$— or R—$[OCH(CH_3)CH_2]_y$— in which R is a linear alkyl radical having 1 to 18 carbon atoms and $1 \leq y \leq 22$, are particularly preferred.

A fourth family of compounds according to the invention comprises salts in which the cationic part $AP^+$ is a polydiazonium represented by Formula (XV):

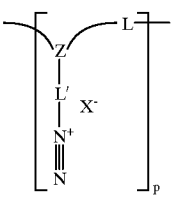
(XV)

in which:

d1) L has the meaning given in paragraph b3) above;

d2) L' has the meaning given in paragraph a2) above;

d3) p represents the number of recurring units, $2 \leq p \leq 1000$;

d4) X represents an anion defined above.

A fifth family of compounds according to the invention comprises organometallic polyonium compounds represented by one of the following Formulae:

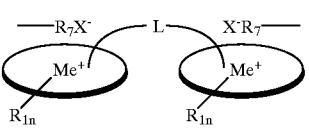
(XVI)

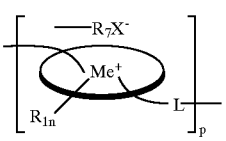
(XVII)

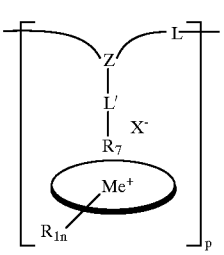
(XVIII)

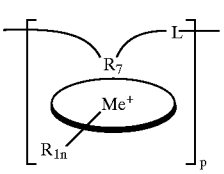
(XIX)

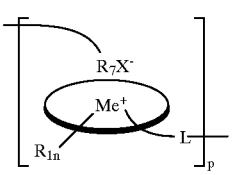
(XX)

in which:

e1) $R_{1n}$ has the meaning given in paragraph b1) above and the substituent $R_7$ is selected from:

linear or branched alkyl or arylakyl radicals having 1 to 30 carbon atoms;

alkenyl radicals having 1 to 30 carbon atoms;

aryl or alkylaryl radicals having 6 to 30 carbon atoms including those which have condensed nuclei;

radicals having 1 to 30 carbon atoms and selected from the group consisting of oxaalkyls, azaalkyls, thiaalkyls, phosphaalkyls, oxaalkylenes, azaalkylenes, thiaalkyls, and phosphaalkylenes;

radicals having 1 to 30 carbon atoms and including a sulfoxide group, a sulfone group, a phosphine oxide group, a phosphonate group, all these radicals being obtained by addition of oxygen on the atoms of sulfur or phosphorus;

aromatic or alicyclic heterocyclic radicals comprising at least one heteroatom selected from the group consisting of O, N, S and P;

—NO, —CN, —OH, —Cl, —Br, —I, —F;

e2) L' has the meaning given in paragraph a2) above;

e3) L has the meaning given in paragraph a3) above;

e4) p represents the number of recurring units, $2 \leq p \leq 1000$;

e5) Z has the meaning given in paragraph a5) above;

e6) X being an anion as defined above;

e7) Me represents a transition metal selected from the transition elements of columns 3 to 12, (lines 3 to 6) of the Periodic Classification.

Examples of compounds in which the cationic part is an organometallic polycation include polymers containing ferrocenium units (in particular those which incorporate the unit vinylferrocene, polyalkylbenzene-iron-cyclopentadiene units), polymers which include nickelocenium units and polymers which include tricarbonyl manganesecyclopentadiene units.

The compounds $(A^+X^-)_p$ of the present invention are in general insoluble in water. They may therefore be prepared by a process consisting in carrying out a metathesis reaction in water or in a water/light alcohol (methanol, ethanol, propanol) mixture between compound $(A^+X_1^-)_p$ which is a soluble salt of the polycation $(A^+)_p$ in which anion $X_1^-$ has a hydrophilic character, and a compound of anion $X^-$ having a highly hydrophilic cation which is soluble in water.

The soluble salts $(A^+X^-)_p$ of polycation $(A^+)_p$, are preferably selected from the salts in which the anion $X_1^-$ is selected from a hydroxide, a chloride, a bromide, a hydrogenosulfate, a dihydrogenophosphate or a methylsulfonate. These anions being highly soluble in water or light alcohols, they promote solubility.

The compounds $(A^+X^-)_p$ of anion $X^-$, which are soluble in water or water/alcohol mixtures, are preferably selected from perhaloalkylsulfonimides and perhaloalkylsulfonylmethanes, perhaloalkyl sulfonimide salts and perhaloalkylsulfonylmethylides of lithium, sodium, potassium, ammonium, calcium or magnesium. The choice of the cation of course depends on the ease of obtention and the minimum of hydrophilic character which is required to produce the solubility.

When the polyionic compound $(A^+X^-)_p$ of the invention is prepared from a salt $(A^+X_1^-)_p$ in which $X_1$ is a chloride, a bromide, an alkylsulfonate, an alkyloxysulfonate or an arylsulfonate, of which the salts of Na or K are insoluble in the usual solvents, it is advantageous to carry out the reaction in the presence of a salt of Na or K or anions $X^-$. The solubility of these salts in the solvents, even those of average polarity, being appreciable, the insoluble salts such as NaCl, KBr precipitate, while the polyionic compound according to the invention remains in solution. As solvents, acetone, methylethylketone, acetonitrile, THF, esters such as formates, methyl or ethyl acetate may be mentioned.

It should be noted that any other process of ionic exchange may be used, for example a process utilizing an ion exchange resin or a process of selective precipitation.

In a surprising manner it has appeared that the polyionic compounds of the invention are soluble in most of the usual organic solvents, contrary to polyionic compounds of the prior art, such as polystyrene-iodonium and polythiaphenyl-sulfonium compounds in spite of high load density. The latter are only soluble in water and highly polar solvents such as dimethylformamide (DMF) or propylene carbonate depending on the type of counter ion. Now, water is incompatible with cationic polymerization reactions and is not a solvent of most of the monomers. Solvents such as DMF or propylene carbonate are very difficult to remove because of their high boiling temperature and they may later on contaminate the materials in contact with products resulting from polymerization/cross-linking (food industry, serigraphies and the like). It was therefore possible to use the polycations of the invention as photoinitiators for cationic polymerization reactions. With respect to ionic monomer compounds, they have a sure advantage: when they are used as photoinitiators, they decompose under the action of actinic radiation without leaving residues capable of migrating in the polymeric phase obtained.

It is consequently an object of the present invention to provide for the use of the polyionic compounds $(A^+X^-)_p$ of the invention as photoinitiators constituting a source of Bronsted acids which are used as catalysts for the polymerization or cross-linking of monomers or prepolymers capable of reacting through a cationic reaction or as catalysts for the modificaqtion of the solubility parameters of polymers. The process of polymerization or cross-linking of monomers or prepolymers which can undergo a cationic reaction is characterized in that a compound of the invention is used as a photoinitiator which constitutes a source of acid which catalyzes the polymerization reaction.

When the polyionic compound of the invention is intended to be used as photoinitiator for the polymerization of monomers or prepolymers which can be polymerized through a cationic reaction, the choice of groups $R_1$ to $R_8$ is made among the above radicals to increase the solubility of said compound in the solvents used with the monomers or prepolymers and as a function of the desired properties for the final polymer. For example, the choice of non-substituted alkyl radicals gives a solubility in media with low polarity. The choice of radicals comprising a group oxa or a sulfone will give a solubility in polar media. The radicals which include a sulfoxide group, a sulfone group, a phosphine oxide group, a phosphonate group obtained by addition of oxygen on the sulfur or phosphorus atoms may give to the polymer obtained improved properties with respect to adhesiveness, brightness, resistance against oxidation or UV.

Monomers and prepolymers which may be polymerized or cross-linked with polyionic photoinitiators of the present invention are those which may undergo a cationic polymerization.

Monomers which may be polymerized or cross-linked with a polyionic compound of the invention used as photoinitiator include monomers which have a cyclic ether function, a cyclic thioether function or a cyclic amine function, vinyl compounds (more particularly vinyl ethers), oxazolines, lactones and lactames.

Among monomers of the cyclic ether or thioether type, ethylene oxide, propylene oxide, exetane, epichlorhydrin, tetrahydrofurane, styrene oxide, cyclohexene oxide, vinyl-cyclohexene oxide, glycidol, butylene oxide, octylene oxide, glycidyl ethers and esters (for example glycidyl methacrylate or acrylate, phenyl glycidyl ether, diglycidyl ether of bisphenol A or its fluorinated derivatives), cyclic acetals having 4 to 15 carbon atoms (for example dioxolane, 1,3-dioxane, 1,3-dioxepan) may be mentioned.

Among the vinyl compounds, vinyl ethers constitute a very important family of monomers sensitive towards cationic polymerization. By way of example, vinyl ethyl ether, propyl vinyl ether, isobutyl vinyl ether, octadecyl vinyl ether, ethyleneglycol monovinyl ether, diethyleneglycol divinyl ether, butanediol monovinyl ether, butanediol divinyl ether, hexanediol divinyl ether, ethyleneglycol butyl vinyl ether, triethyleneglycol methyl vinyl ether, cyclohexanedimethanol monovinyl ether, cyclohexanedimethanol divinyl ether, 2-ethylhexyl vinyl ether, poly-THF-divinyl ether of molecular weight between 150 and 5000, diethyleneglycol monovinyl ether, trimethylolpropane trivinyl ether, aminopropyl vinyl ether, 2-diethylaminoethyl vinyl ether, may be mentioned.

Also included are methyl vinyl ethers which contain one or more $CH_3CH=CH—0—$ groups and which are advantageously obtained by isomerization of corresponding allyl ethers in the presence of a catalyst such as $(\Phi_3P)2RuCl_2$.

Other vinyl compounds which may undergo cationic polymerization in the presence of a polyionic compound of the invention when used as photoinitiator may include by way of example 1,1-dialkylethylenes (for example isobutene), vinyl aromatic monomers (for example styrene, α-alkylstyrenes, such as α-methylstyrene, 4-vinylanisol, acenaphtene), and vinyl compounds (for example N-vinylpyriolidone, N-vinyl formamide or N-vinyl sulfonamides).

Among the prepolymers, compounds in which the epoxy groups are carried by an aliphatic chain, an aromatic chain or a heterocyclic chain, for example glycidyl ethers of bisphenol A which are ethoxylated with 3 to 15 ethylene or propylene oxide units, siloxanes having lateral groups of the type epoxycyclohexene-ethyl obtained by hydrosilylation of copolymers of dialkyl, alkylaryl or diaryl siloxane with methyl hydrogenosiloxane in the presence of vinylcyclohexene oxide, or difimctional unsaturated ethers possessing a vinyl ether end and a methylvinyl ether end (propenyl), condensation products of the type sol-gel obtained from triethoxy or trimethoxy silapropylcyclohexene oxide, urethanes incorporating the reaction products of butanediol monovinyl ether and an alcohol of a functionality higher than or equal to 2 with an aliphatic or aromatic di- or triisocyanate, may be mentioned.

The process of polymerization according to the invention consists in mixing at least one monomer or prepolymer capable of cationic polymerization and at least one ionic compound $AP^+pX^-$ of the invention and treating the mixture obtained with actinic or β-radiation. Preferably, the reaction mixture is subject to radiation after having been formed into a thin layer of a thickness lower than 5 mm, preferably in the form of a thin film having a thickness lower than or equal to 500 μm, The length of the reaction depends on the thickness of the sample and of the power of the source at the active wavelength λ. It is defmed by the speed at which it passes in front of the source, which is between 300 m/min and 1 cm/min. Layers of the final material having a thickness higher than 5 mm may be obtained by repeating a number of times the operation consisting in spreading a layer and treating it with radiation.

Generally, the quantity of polyionic photoinitiator $AP^+pX^-$ used is between 0.01 and 15% by weight with respect to the weight of the monomer or the prepolymer, preferably between 0.1 and 5% by weight.

A polyionic compound $(A^+X^-)_p$ of the present invention may be used as photoinitiator in the absence of solvent, for example when it is desired to polymerize liquid monomers in which the salt is soluble or easily dispersible. This type of utilization is particularly interesting since it enables to overcome problems associated with solvents (toxicity, flammability).

A polyionic compound $(A^+X^-)_p$ of the present invention may also be used as photoinitiator in the form of a homogeneous solution in a solvent which is inert towards polymerization, which is ready to be used and is easily dispersible, in particular in the case where the mixture to be polymerized or cross-linked has a high viscosity.

As example of inert solvents, volatile solvents, such as acetone, methylethyl ketone and acetonitrile may be mentioned. These solvents will simply serve to dilute the products to be polymerized or cross-linked (to render them less viscous, especially when a prepolymer is involved). They will be removed by drying after polymerization or crosslinking. Non-volatile solvents may also be mentioned. A non-volatile solvent has the same use as a volatile solvent, that is to dilute the products which are intended to be polymerized or cross-linked and to dissolve the polyionic compound $(A^+X^-)_p$ of the invention when used as photoinitiator, but in addition it will remain in the material obtained and will thus act as plasticizing agent. By way of example, propylene carbonate, γ-butyrolactone, ether-esters of mono-, di-, triethylene or propylene glycols, ether alcohols, mono-, di-, triethylene or propylene glycols, plasticizing agents such as phthalic acid or citric acid may be mentioned.

According to another embodiment of the invention, the solvent or diluent used is a compound which is reactive towards polymerization, has a low molecular weight and low viscosity which will act simultaneously as polymerizable monomer and solvent or diluent for more viscous monomers or prepolymers jointly used. After the reaction, these monomers which have been used as solvent are part of the macromolecular network finally obtained, their integration being greater when bifunctional monomers are present. The material obtained after radiation is free of products having a low molecular weight and an appreciable vapor pressure, or which are susceptible of contaminating the object with which the polymer is in contact. By way of example, a reactive solvent may be selected from vinyl mono- and diethers or mono-, di-, tritetraethylene and propylene glycols, N-methylpyrolidone, 2-propenylether of propylene carbonate commercially sold for example under the trade designation PEPC by ISP, New Jersey, U.S.A.

To radiate the reaction mixture, the radiation may be selected from ultraviolet radiation, visible radiation, X-rays, γ-rays, and β-radiation. When ultraviolet light is used as actinic radiation it may be advantageous to add to the photoinitiators of the invention, photosensitizers intended to permit an efficent photolysis with less energetic wavelengths than those corresponding to the maximum of absorption of the photoinitiator, such as those emitted by industrial devices ($\lambda \approx 300$ nm for mercury vapor lamps in particular). Such additives are known, and by way of non-limiting examples, anthracene, diphenyl-9,10-anthracene, perylene, phenothiazine, tetracene, xanthone, thioxanthone, acetophenone, benzophenone, 1,3,5-triaryl-2-pyrazolines and their derivatives, in particular the derivatives which are substituted on the aromatic nuclei by means of alkyl, oxa- or aza-alkyl radicals enabling among other to change the absorption wavelength may be mentioned. Isopropylthioxantone is an example of photosensitizer when a polyiodonium compound $AP^+pX^-$ of the invention is used as a photoinitiator.

Among different types of radiations mentioned, ultraviolet radiation is particularly preferred. On the one hand it is easier to use than the other mentioned radiations. On the other hand, photoinitiators are in general directly sensitive towards UV radiations and the photosensitizers are more especially efficient when the difference of energy ($\delta\lambda$) is smaller.

The polyionic compounds $(A^+X^-)_p$ of the invention may also be used in association with initiators of the radical type which are produced with heat or actinic radiation. It is thus possible to polymerize or cross-link mixtures of monomers or prepolymers containing functions in which the modes of polymerization are different, for example, monomers or prepolymers which polymerize by free radical reaction and monomers or prepolymers which polymerize by cationic reaction. This possibility is particularly advantageous when it is intended to produce interpenetrated networks having physical properties which are different from those which would be obtained by simple mixture of the polymers originating from corresponding monomers. Vinyl ethers are not or very little active by radical initiation. It is therefore possible in a reaction mixture containing a photoinitiator according to the invention, a free radical initiator, at least one monomer of the vinyl ether type and at least one monomer comprising non-activated double bonds such as those of allyl groups, to carry out a separate polymerization for each type of monomer. It is on the other hand known that electron lacking monomers, such as esters or amides of fumaric acid, maleic acid, acrylic or methacrylic acid, itaconic acid, acrylonitrile, methacrylonitrile, maleimide and its derivatives, form in the presence of vinyl ethers rich in electrons, charge transfer complexes giving alternate polymers 1:1 by radical initiation. An initial excess of vinyl monomers with respect to this stoichiometry enables to preserve polymerizable functions by pure cationic initiation. The setting in motion of the activity of a mixture of a free radical initiator and a cationic initiator according to the invention may be carried out simultaneously for the two reactants in the case of, for example, a treatment with actinic radiation at a wavelength in which the photoinitiators of the invention and the free radical initiators selected are active, for example at $\lambda=250$ nm. By way of example, as initiators, the following commercial products: Irgacure 184®, Irgacure 651®, Irgacure 261®, Quantacure DMB®, Quantacure ITX® may be mentioned.

It may also be advantageous to use the two modes of polymerization in a sequential manner to first produce prepolymers which are easy to obtain and in which the hardening, adhesiveness, solubility, as well as the degree of cross-linking may be modified by activating the cation initiator. For example, a mixture of a thermodissociable free radical initiator and a cationic photoinitiator according to the invention enables to obtain sequential polymerizations and cross-linkings, first under the action of heat and then under the action of an actinic radiation. In a similar manner, if a free radical initiator and a cationic photoinitiator according to the invention are selected, the first being photosensitive towards longer wavelengths than the one produced by the photoinitiator according to the invention, there is obtained a cross-linking in two controllable steps. Free radical initiators may, for example, include Irgagure® 651 enabling to initiate free radical polymerizations at wavelengths of 365 mn.

It is also an object of the invention to provide polyionic compounds $(A^+X^-)_p$ of the invention for reactions of chemical amplification of photoresists for microlithography. During one such utilization a film of a material comprising a polymer and a polyionic compound $(A^+X^-)_p$ of the invention is subject to radiation. The radiation causes the formation of the acid HX which catalyzes the decompositon or conversion of the polymer. After decomposition or conversion of the polymer on parts of the film which have been radiated, the monomer formed or the converted polymer are removed and one is left with a picture of the non-exposed parts. For this particular application it is advantageous to use polymers comprising vinyl units having an ionic substituent. Among these compounds polyiodonium salts represented by Formula (III), salts of polysulfonium represented by Formula (VI), polyacylsulfonium represented by Formula (XI), polydiazonium compounds represented by Formula (XV), salts of organometallic complex represented by Formula (XVIII) may be mentioned. After photolysis, these compounds enable to obtain products which are non-volatile and therefore without smell when sulfides are concerned. Among the compounds of the invention, polysulfonium which are particularly efficient as photoinitiator, phenacylsulfonium compounds and polymers and copolymers of viyl ferrocenium which may easily be obtained, are particularly preferred. Among the polymers which may thus be modified in the presence of a compound of the invention, the following are, for example, mentioned: monomers containing ester groups or tertiary alcohol arylether groups, for example poly (phthalaldehydes), polymers of bisphenol A and of a diacid, polytertiobutoxycarbonyl oxystyrene, polytertiobutoxy-α-methyl styrene, polyditertiobutyl-fumarate-co-allyltrimethylsilane and polyacrylates of a tertiary alcohol, in particular tertiary butyl polyacrylate. Other plymers are described in J. V. Crivello et al., Chemistry of Materials 8, 376–381 (1996).

The polyionic compounds $(A^+X^-)_p$ of the present invention which have a high heat stability offer many advantages with respect to the salts known in the prior art. They have initiation and propagation speeds which are comparable or higher than those obtained by coordination of anions of the type $PF_6^-$, $AsF_6^-$ and especially $SbF_6^-$. The salts $M^+X^-$ in which M is an alkali metal and X is an anion which is identical to the anion of a compound of the present invetion are known to be easily soluble in the polymers, of which they only slightly increase the glass transition temperature. In addition, the coefficient of diffusion of the anion $X^-$ is higher than that of hexafluorometallate, tetrafluoroborate or phenylborate anions. These properties are explained by a delocalization of the negative charge and a flexibility of the anion around the bounds SNS or SCS.

Another interesting advantage of the polyionic compounds $(A^+X^-)_p$ of the invention is the absence of toxic elements such as P, As or Sb, these elements being on the other hand considered as contaminating agents in processes of microelectronics.

The possibility of modifying the solubility parameters and the melting temperatures of the salts of the invention by the choice of groups $R_F$, $R'_F$ as well as Q defined above, adapted to the polarity of the medium used for polymerization, cross-linking or chemical amplification reactions, should also be mentioned. The very low superficial tension which characterizes perfluorated groups, confers to the polyionic compounds $(A^+X^-)_p$ of the invention tensioactive properties useful for the mixture and the homogeneous dispersion of pigments and charges in the polymerizable mixtures.

The present invention is described hereinafter more in detail by means of the following examples which are given by way of illustration, the invention not being limited to these examples.

EXAMPLE 1

Preparation of a poly(indonium) salt: the aromatic nuclei of a sample of polystyrene ($M_w$ 6000) are converted into a iodophenyl group par iodation of polystyrene, oxidation into iodosoacetate with a mixture of acetic acid, acetic anhydride and hydrogen peroxide according to the method of Yamada et al. (*Die Makromolecular Chemie*, (1972) 152, 153–162). 10 of the thus prepared compound are placed in suspension in a mixture of 30 mL methanesulfonic acid and 5 mL butoxybenzene maintained at 0° C. during 4 hours. The reaction product is poured into 400 mL of a mixture 2:1 v/v ether:isopropanol and the precipitate is separated by filtration, washed with THF and dried. 8 g of the polyiodonium methanesuylfonate thus obtained are suspended in 50 mL water and 10 g of the salt lithium bis(nonafluorobutanesulfonyl)imide in solution in 25 mL water are added. The mixture is stirred during 1 hour and is separated by filtration. The yield of ionic exchange (metathesis) is quantitative to give bis(nonafluorobutanesulfonyl)imide of poly(vinylphenyl-(4-butoxyphenyl)-4-iodonium.

The structure of the polymer is:

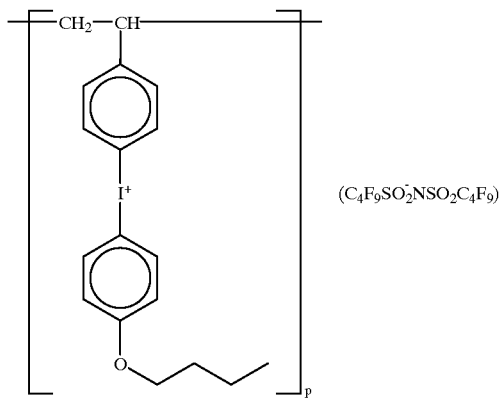

EXAMPLE 2

Preparation of a poly(sulfonium) salt from a polyiodonium salt: 3 g of the polyionic compound of Example 1 are mixed with 5 mL of 4-butylphenylthioether and 500 mg of copper benzoate, finely dispersed and heated at 130° for three hours in molten phase. At the end of the reaction, the mixture is dissolved in 30 mL acetone and is precipitated in 100 mL ether. The process of purification is repeated three times, in the system acetone (solvent)/water (precipitant). The following polysulfonium salt is obtained:

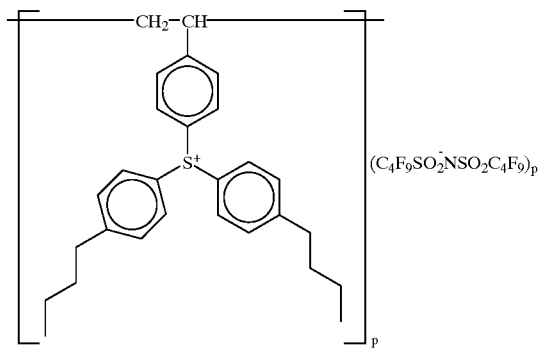

The solubility parameters of the two polymers of examples 1 and 2 are summarized in the following table:

| Solvent | Acetone | $C_2H_4Cl_2$ | MEK | DVE-3 | PC |
|---|---|---|---|---|---|
| Example 1 [$I^+$] | soluble | s | s | s > 5% | s |
| Example 2 [$S^+$] | soluble | s | s | s > 5% | s | s= soluble > 20% w/w
DVE3= triethylene glycol divinyl ether
MEK= methylethylketone
PC= propylene carbonate The exceptional solubility character of polyelectrolytes having a high density of charge is thus established.

EXAMPLE 3

A polymer similar to that of example 1 but with a methoxy group instead of butoxy may be obtained by following the operating method of Crivello & Lee (U.S. Pat. No. 4,780,511) by reacting poly(4-iodostyrene) (23 g) with anisole (10.8 g) in the presence of peracetic acid (45.6 g) and toluenesulfonic acid (19.05 g) in dichloromethane (40 mL). 25 g of the polymer obtained are dispersed in a mixture 1:1 of ethanol and acetone to which are added 15 g of the salt bis(trifluoromethanesulfonyl)imide. The viscous solution is centrifuged to eliminate sodium toluenesulfonate and is precipitated in water in the form of a yellow powder which is soluble in the usual solvents.

EXAMPLE 4

The compound phenoxyethylvinylether is prepared by reacting chloroethylvinylether with sodium phenate, followed by polymerization in dichloromethane initiated with $TiCl_4$ at −10° C. By reacting 8.2 g of the polymer with 9.8 g of phenyliodosotoluene sulfonate in 40 mL of a mixture of an equal volume of acetic acid and dichloromethane. A polyiodonium is obtained which is precipitated with ether. The ionic exchange reaction is carried similarly to that of example 3 between 12 g of polymer and 7 g of sodium bis(trifluoromethanesulfonyl)imide. After precipitation and washing with water, there is obtained a sticky mass which is used in a 50% solution of methylethylketone.

EXAMPLE 5

An oligomer containing iodonium groups is prepared according to the method described in *J Polym. Sci., Polym. Lett.* (1976), 14, 65 in the form of bromide. 4 g of this oligomer are placed in solution in 50 mL of water to which there is added 5 g of sodium tris(trifluoromethanesulfonyl)methylide dissolved in 25 ml of water. The precipitate is separated by filtration. This material is soluble in the usual polar solvents such as acetone or monomers such as (4-propenyloxymethylene) 1,3-dioxolane-2-one (PEPC from International Specialty Producxts, Wayne N.J., USA). The polyiodonium associated to the bromide ion has only a negligible solubility in the best known polar solvents. (DMSO, DMF, HMPA).

EXAMPLE 6

The solubility properties conferred to polyelectrolytes associated to the anions according to the the present invention are illustrated hereinafter by comparison with the properties of a poly(iodonium) prepared according to Crivello & Lam (*J. Polym. Sci.; Polymer Chemistry*, (1979), 17 3845–3858) by trans-addition of (4,4'-N-maleimido) diphenyliodonium with 1,10-decanethiol in m-cresol in the presence of a tertiary base. By metathesis in the presence of different salts, the following poly(iodonium) have been tested for solubility:

| Anion Solvent | Acetone | $C_2H_4C_2$ | MEK | NMP | PEPC |
|---|---|---|---|---|---|
| $(CF_3SO_2)_2N^-$ | soluble | s | s | S | s |
| $(CF_3SO_2)N(SO_2C_4F_9)^-$ | s | s | s | s | s |
| $(CF_3SO_2)_3C^-$ | s | s | s | s | s |
| polymer-$PF_6$ | insoluble | i | i | i | i |

EXAMPLE 7

A polythioether is prepared by reacting 15 g of dimer-captohexane with 18.67 g of 1,2-bis(2-chloroethoxy)ethane in 200 mL of N-methylpyrolidone at 150° C. in the presence of 10 g of potassium carbonate. The polymer is precipitated in water and purified in many solubilizing operations ($CH_2Cl_2$)/precipitation (diethylether) and separation by centrifugation in a single container. The polymer is in the form of a sticky mass. In a three-neck flask provided with a cooler, a mechanical stirrer and a neutral gas inlet (Ar), 7 g of the polymer are dissolved in 120 mL of dichloromethane ($CH_2Cl_2$) and 4.8 of 2-bromoacetophenone are added dropwise. The mixture is heated under reflux at 40° C. A precipitate rapidly appears. The reaction is continued 12 hours after the appearance of the precipitate. Polyphenacylsulfonium bromide is separated by filtration and washed with dichloromethane and ether. 5 g of the poly(salt) are dissolved in 60 mL of water, the solution is filtrated and to this 3 g of the lithium salt of bis-(triifluoromethanesulfonyl)imide ($Li[CF_3SO_2]_2N$) in 25 mL of water are added; a precipitate is immediately formed and stirring is continued during 1 hour. The polymer is separated by filtration and dried (quantitative yield). By comparison, the same preparation is carried out and precipitation is carried out in the presence of 2.2 g of sodium hexafluorophosphate. The properties of solubility are summarized by way of illustration in the following table:

| solvant | Acétone | $C_2H_4Cl_2$ | MEK | DVE-3 | E/DVE3 |
|---|---|---|---|---|---|
| polymer-imide | soluble | s | s | s > 3% | s > 3% | c= compatible (absence of micro-separation of optically visible phase)
DVE3= triethylene glycol divinyl ether
E= Epoxide (bisphenol A diglycidylether)

EXAMPLE 8

A polythioether similar to that of the preceding example is prepared by reacting 8 g of 2-mercaptoethylether with 15.3 g of α,α-dibromo-m-xylene in 100 mL dimethylformamide at 80° C. in the presence of 4 g of potassium carbonate. The polymer is precipitated in water and purified as previously. In a three-neck flask provided with a cooler, a mechanical stirrer and a neutral gas inlet (Ar), 10 g of the polymer are dissolved in 120 mL hexane and 11.5 g of bromoacetyl-4-octyloxy-benzene are added dropwise. The mixture is heated under reflux at 60° C. A precipitate appears rapidly. The reaction is continued 12 hours after the appearance of the precipitate. Polyphenacylsulfonium bromide is separated by filtration and washed with hexane and ether. 7 g of the poly(salt) are suspended in 60 mL acetone and under stirring there are added 5.15 g of a potassium salt of tris(trifluoromethanesulfonyl)methane ($K[CF_3SO_2]_3C$. The reaction mixture is maintained under stirring during 1 hour at room temperature, and the solution is filtrated to eliminate the potassium bromide formed; acetone is evaporated to leave a very viscous mass of the polyionic compound.

| Solvent | Acetone | $C_2H_4Cl_2$ | MEK | DVE-3 | Epoxy/VGE |
|---|---|---|---|---|---|
| Salt octyloxy | □ | □ | □ | s > 10% | s > 10% |

| Solvent | toluene | BVE-1 | photo-1 | PDMS 10 | PDMS 500 |
|---|---|---|---|---|---|
| Salt octyloxy | s | s | c > 1% | s > 2% | s > 1% |

E= bisphenol A of diglycidylether
DVE3= methylene glycol divinyl ether
BVE-1= butanediolmonovinylether
photo-1= resin for resist with chemical amplification: poly(t-butoxycarboxystyrene-co-cyanoethylacrylate) 1:1
PDMS 10= α,ω-trimethylsiloxy-polydimethylsiloxane: viscosity 10 cSt, $M_W$ ≈ 1250
PDMS 500= ditto: viscosity 500 cSt, $M_W$ ≈ 17250
E/VGE= 50 v/v bisphenol A diglycidylether, triethylene glycol divinyl either

EXAMPLE 9

6.5 g of trifluoromethanesulfonamide $CF_3SO_2NH_2$ and 10.8 mL of pyridine in 60 mL of dichloromeithane are cooled at −15° C. and 3.6 mL of sulfuryl chloride in 10 mL of dichloromethane and 4.6 mL of 1,1,1,3,3,3-hexafluoro-2-propanol are added dropwise. The misture is stirred during 1 hour at −15° C., then 4 hours at room temperature (25° C). The reaction mixture is filtrated and the solvent is eliminated with a rotary evaporator. The solid residue is dissolved in 50 mL water containing 5 g of sodium acetate and 18.45 g of finely divided bis(hexafluorophosphate) of bis [4-(diphenylsulfonio)-phenyl]thioether (prepared according to the method of Akhtar et al. (*Chem. Mat.* (1990), 2, 732 and K. T. Chang. U.S. Pat. No. 4,197,174) are added and the mixture is stirred at room temperature during 3 hours in a roller crusher of rigid polyethylene zirconium containing oxide balls. The suspension obtained is filtrated and the solid obtained is dried. There is obtained 28 g (78%) of the compound of the following structure:

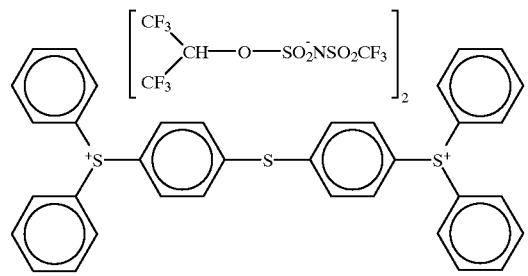

EXAMPLE 10

To 4 g of the dimer cyclopentadienyl-iron-dicarbonyl (Aldrich, Milwaukee, USA) dissolved in 20 mL of acetonitrile and maintained a 0° C., there is added—while maintaining a strong stirring—0.58 mL of bromine diluted in 5 mL of acetonitrile; the reaction of formation of the salt $CpFe(CO)_2Br$ is immediate and quantitative. 20 g of 2-isopropenyl-4-cumene (p-isopropyl-styrene) are polymerized in 200 mL of dichloromethane at −10° C. by cationic initiation with 150 μL of $SnCl_4$. The polymer precipitates in ether and is purified through a plurality of dissolving ($CH_2Cl_2$)/precipitation (diethylether) operations. The polymer yield is 63% in the form of a white solid. In a three-neck flask provided with a cooler, a mechanical stirrer and a neutral gas inlet (Ar), 8.2 g of the polymer are dissolved in 120 mL of dichloroethane ($C_2H_4Cl_2$) and the solution of $CpFe(CO)_2Br$ in acetonitrile previously prepared is added. The mixture is heated under reflux. A precipitate appears with concomitant release of carbon monoxide. The reaction is continued 2 hours after the appearance of the precipitate. The poly(areneferrocenium) bromide is separated by filtration and washed with dichloromethane and acetonitrile. 3 g of the polyionic compound are dissolved in 50 mL water to which are added 3.8 g of the lithium salt of (nonafluorobutanesulfonyl)-trifluoromethylsulfonyl)-imide ($Li[C_4F_9SO_2NSO_2CF_3]$ in 25 mL of water; a precipitate is immediately formed and stirring is continued during 1 hour. The polymer is separated by filtration and dried (quantitative yield). By comparison, the same preparation is carried and the precipitation is carried in the presence of 1.5 g of sodium hexafluorophosphate. Comparison of the properties is summarized in the following table:

| Solvent | Acetone | $C_2H_4CL_2$ | MEK | DVE-3 | PC |
|---|---|---|---|---|---|
| Polymer-imide | soluble | s | s | s > 3% | s |
| Polymer-$PF_6$ | insoluble | i | i | i | s |

DVE3= triethylene glycol divinyl ether
PC= propylene carbonate

EXAMPLE 11

3.4 g of [bis(trifluoroacetoxy)iodo]benzene are added to 5 g of 1,2-diferrocenylethane (Aldrich Co. Milwaukee, USA) in solution in 50 mL of toluene. A blue precipitate is immediately formed and is separated, washed with ether and dried. 5 g of this solid 624.14724 are placed in solution in 25 mL of water and 4.9 g of sodium bis (trifluoromethanesulfonyl)imide are added thereto. The prcipitate of the ferrocene dimer in the form of salt of the imide anion is obtained with a quantitative yield in the form of a crystalline blue powder.

EXAMPLE 12

To 6 g of a copolymer of vinylferrocene (Aldrich Co. Milwaukee, USA) and butyl methacrylate containing 42% organometallic units obtained by free radical polymerization induced by azobis(butyronitrile) in solution in toluene are added 3.3 g of [bis-(trifluoroacetoxy)iodo]benzene (Aldrich). A blue precipitate is immediately formed and is separated, washed with ether to remove the excess of dried oxidizing agent. 5 g of this poly(salt) of ferricinium associated to the trifluoroacetate anion are suspended in 25 mL water to which are added 3 g of sodium bis (trifluoromethanesulfonyl)imide. The precipitate of the polysalt of the imide anion of the polyferricinium is obtained with a quantitative yield in the form of a blue amorphous powder which is soluble in most usual solvents.

EXAMPLE 13

In a three-neck flast equipped with a cooler, a mechanical stirrer and a neutral gas inlet (Ar), 9.5 g of a copolymer of dimethylsiloxane and of (hydrogeno)(methyl)-siloxane (HMS 301 25% SiH, $M_w$ 1900 Gelest Inc., Tullytown, Pa., USA) are placed in solution in THF; 7.9 g of allylferrocene and 70 mg of chloroplatinic acid $H_2PtCl_6$ are added. The irixture is heated under reflux during 4 hours. A sampling enables to confirm the complete disappearance of IR bands of the bond SiH. The polymer is precipitated in methanol and is purified by three operations of dissolution (THF)/ precipitation (methanol). To 5.4 g of this polymer in solution in dichloromethane are added 2.4 g of [bis(trifluoroacetoxy) iodo]benzene. The reaction product is poured in 100 mL ether and the precipitate is separated by centrifugation. Metathesis enabling to replace the trifluoroacetate anion by the tris(trifluoromethanesulfonyl)methylide anion is carried out in water (1 mL) between 4.2 g of the poly(cation) and 3.1 g of the salt sodium tris(trifluoromethanesulfonyl)- methylide dissolved in 25 mL water. The polymer is separated by centrifugation and is in the form of a gummy blue mass which is soluble in most solvents, including in quantities >3% in silicone oils. The structure of the polymer is the following:

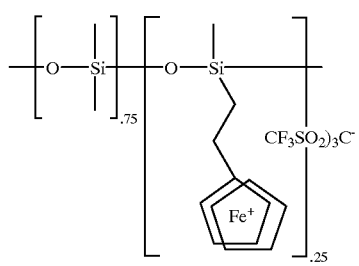

EXAMPLE 14

An oligomer of diazonium is prepared according to the method known and discussed in U.S. Pat. No. 2,714,066, by condensation of 4-diazodiphenylamine chlorozincate. 25 g of this poly(salt) are dissolved in 500 mL water maintained at 0° C. and containing 50 g of sodium acetate and 28 g of a di-salt of sodium of ethylene diamine tetraacetic acid (EDTA). 24 g of the sodium salt of bis (trifluoromethanesulfonyl)imide in solution in 50 mL water are then added. The poly(salt) is separated by filtration and dried (quantitative yield) and kept at 0° C. away from light. This compound is very soluble in the usual organic solvents of average polarity such as MEK and soluble in monomers of the type DVE-3 or PEPC, glycidyl ethers.

EXAMPLE 15

Negative photoresist: 2 g of poly(4-hydroxystyrene)-co- styrene (8.2) Shinetsu, Japan) in solution in 20 mL dimethylformamide are added to 9.7 mL of a 1M solution of potassium hydroxide in methanol and 1.2 g of chloroethylvinylether. The solution is heated at 80° C. during 1 hour and the reaction mixture is poured in 100 mL water where the poly(4-vinyloxyethyl)-styrene formed precipitates. The polymer is purified by many operations of dissolution precipitation in acetone (solvent)/water (precipitant) and acetone (solvent)/ether (precipitant). 1 g of poly(4- vinyloxyethyl)-styrene-co-styrene and 20 mg of the polymer of example 1 in 10 mL MEK are spin-coated on a substrat of silicon so as to form a film 0.5 μm thick (by an exposition of 1MJ/cm2 obtained with a KrF laser through an interferential mask). The development is carried out with THF. The resolution obtained, observed with an electronic microscope (SEM) is of the order of the thickness of the film, i.e. 0.5 μm. This photoresist contains no metallic element capable of contaminatin silicon.

EXAMPLE 16

Positive photoresist: 1 g of poly(4-t- butoxycarboxystyrene) in dichloroethane and 60 mg of the polymer of example 8 are spin coated on a substrate so as to form a film 0.5 mm thick with an exposition 1MJ/cm2 obtained with a KrF laser through an interferential mask. Development is carried out with a 4% solution of tetramethyl ammonium hydroxide in water. The resolution obtained, observed with an electronic microscope (SEM) is of the order of the thickness of the film, i.e. 0.5 $\mu$m. This photoresist contains no metallic element capable of contaminating silicon.

EXAMPLE 17

The properties of photo-initiation of the products of the invention are illustrated in the following table. The polyionic compounds of the preceding examples are used at 4% by weight in various monomers and irradiated by a UV radiation at 254 nm with a power of 1900 mW/cm$^2$ for 5 seconds followed by a period of 10 minutes enabling to propagate species produced in the medium (postcure).

| Monomer__ __Photo- initiator | DVE3 | Epoxy + DVE3 | CHDM + 10% PEPC | cyclohexene- epoxyde polysiloxane-* | $\alpha$- methyl- styrene |
|---|---|---|---|---|---|
| Ex. 1 | ++ | ++ | + | | |
| Ex. 2 | ++ | ++ | + | + | + |
| Ex. 3 | ++ | ++ | + | | |
| Ex. 4 | ++ | ++ | + | + | |
| Ex. 5 | ++ | ++ | + | | |
| Ex. 6 | ++ | ++ | + | | |
| Ex. 7 | ++ | ++ | + | + | + |
| Ex. 8 | ++ | ++ | + | + | + |
| Ex. 9 | ++ | ++ | + | + | + |
| Ex. 10 | ++ | ++ | + | + | + |
| Ex. 11 | ++ | ++ | + | + | + |
| Ex. 12 | ++ | ++ | + | + | |
| Ex. 13 | ++ | ++ | + | + | + |
| Ex. 14 | ++ | ++ | + | + | |

*cross-linking
++very exothermic polymerization giving colored polymer
+polymerization giving a non sticky resin

We claim:

1. Polymer or oligomer ionic compound made of polycationic part (A+)p comprising onium units and anions X$^-$ providing electrical neutrality to the compound, wherein:

the onium units are selected from the group consisting of biaryliodonium, arylsulfonium, arylacylsulfonium, diazonium, organometallic cations comprising a transition metal which is complexed by at least one aromatic or polyunsaturated cycle comprising 4 to 12 carbon atoms;

X$^-$ is an imide anion [R$_F$SO$_2$NSO$_2$R'$_F$]$^-$ or a methylide anion [R$_F$SO$_2$C(Q)SO$_2$R'$_F$]$^-$ in which:

1) Q represents:
H—, Cl—, F—, Br— or CN—;
an alkyl radical having 1 to 30 carbon atoms;
an aryl, alkylaryl or arylakyl radical having 6 to 30 carbon atoms;
a group R"$_F$ or a group R"$_F$SO$_2$;

2) R$_F$ and R'$_F$, as well as R"$_F$ when X$^-$ is a methylide anion, are independently selected from the group consisting of fluorine, a perhaloalkyl group having 1 to 30 carbon atoms, a (perhaloalkyl)alkyloxy group, a halogenated cycloaliphatic group having 3 to 30 carbon atoms and a perhalogenated aryl having 6 to 30 carbon atoms; or 3) R$_F$ and R'$_F$ together from a bivalent radical constituting a cycle respectively with group —SO$_2$—N— SO$_2$— or with group —SO$_2$—C(Q)—SO$_2$—, or when X$^-$ is a methylide anion, R"$_F$ constitutes with one the radicals R$_F$ or R'$_F$ a bivalent radical constituting a cycle respectively with group —SO$_2$—C— SO$_2$— or with group —SO$_2$—C—, said bivalent radical being selected from the group consisting essentially of a perfluorinated alkylene radical having 2 to 12 carbon atoms, R"$_F$ being selected from the group consisting essentially of the monovalent radicals mentioned above in 2);

4) p represents the number of onium units.

2. Ionic polymer according to claim 1 wherein the anion is a sulfonimide [R$_F$SO$_2$NSO$_2$R'$_F$]$^-$ or a sulfonylmethylide [R$_F$SO$_2$C(Q)SO$_2$R'$_F$]$^-$ in which:

Q is selected from the group consisting of alkyl, aryl, alkylaryl or arylakyl groups having at most 30 carbon atoms, a perfluoroalkylsulfonyl group having 1 to 8 carbon atoms and a perfluoroalkyl radical having 1 to 12 carbon atoms;

R$_F$ and R'$_F$ being independently selected from the group consisting of a perfluoroalkyl group having 1 to 10 carbon atoms; or R$_F$ and R'$_F$ together form a linear perfluoroalkylene radical having 1 to 8 carbon atoms.

3. Ionic polymer according to claim 1 comprising a salt of polyiodonium represented by one of the following Formulae (I) to (IV), or a polysulfonium salt represented by one of the following Formulae (V) to (IX), or a polyacylsulfonium salt represented by one of the following Formulae (X) to (XIV), or a polydiazonium salt represented by the following Formula (XV), or an organometallic polyonion salt represented by one of the following Formulae (XVI) to (XX):

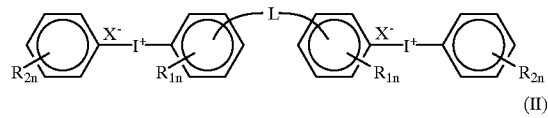
(I)

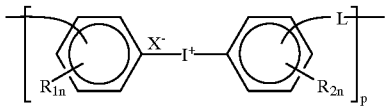
(II)

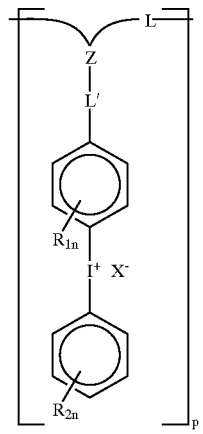
(III)

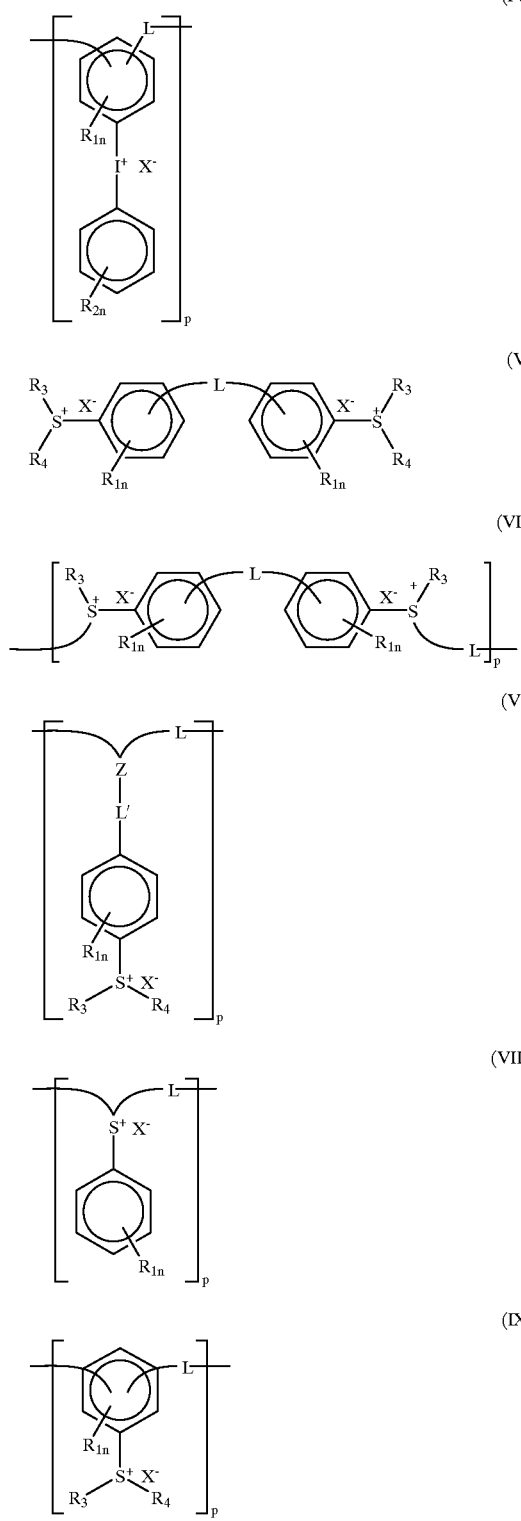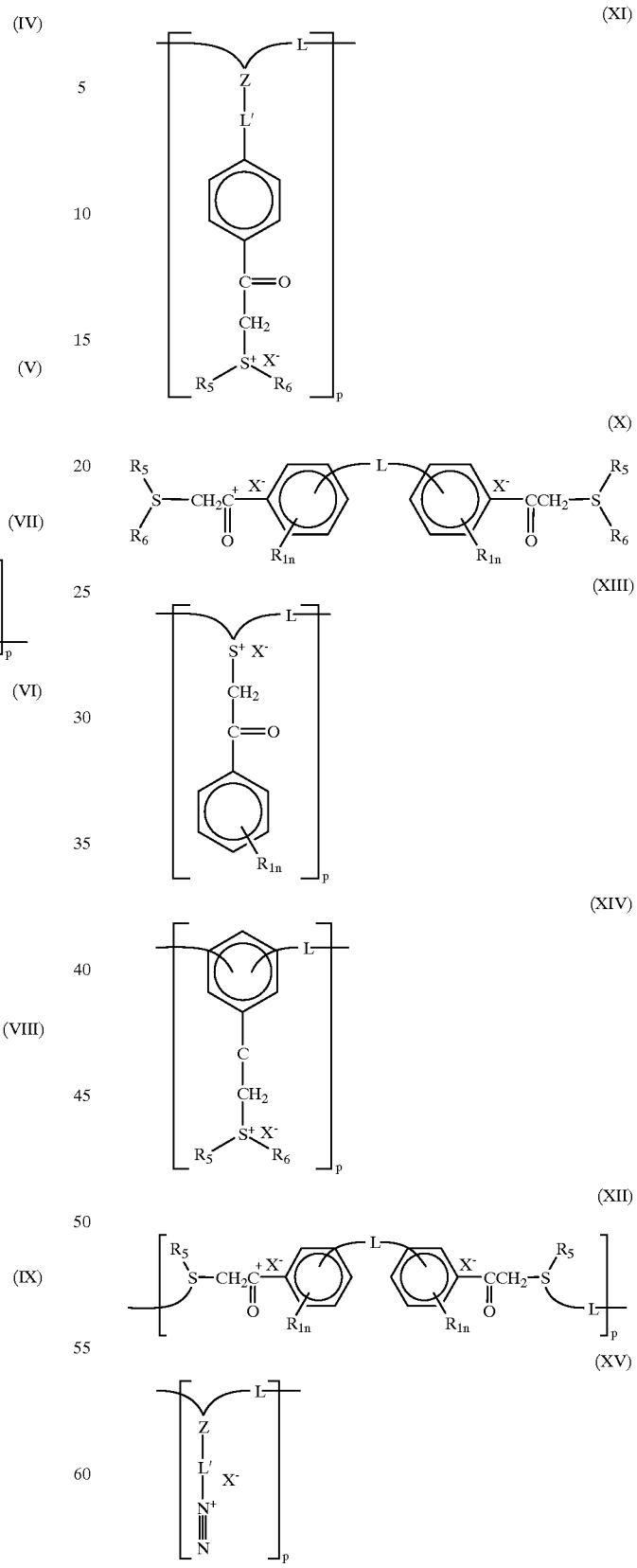

(XVI)

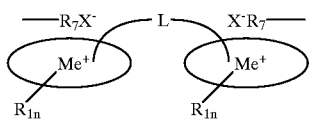

(XVII)

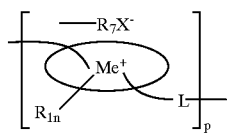

(XVIII)

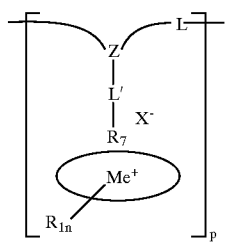

(XIX)

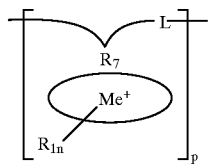

(XX)

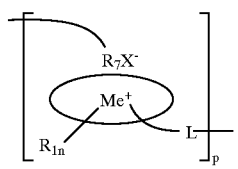

in which:
- a1) $R_{1n}$ represents 1 to 4 groups which are identical or different and are bound to any free carbon atom of the aryl group, $R_{2n}$ represents 1 to 4 groups which are identical or different and are bound to any free carbon atom of the aryl group, the $R_{1n}$ and $R_{2n}$ groups as well as $R_3$ to $R_8$ groups being independently selected from:
  - linear or branched alkyl or arylalkyl radicals having 1 to 30 carbon atoms;
  - alkenyl radicals having 1 to 30 carbon atoms;
  - aryl or alkylaryl radicals and aryl or alkylary radicals having condensed nuclei having 6 to 30 carbon atoms;
    - radicals having 1 to 30 carbon atoms selected from the group consisting of oxaalkyl, azaalkyls, thiaalkyls, phosphaalkyls, oxaalkylenes, azaalkylenes, thiaalkylenes and phosphaalkylenes;
    - radicals having 1 to 30 carbon atoms selected from the group consisting of a sulfoxide group, a sulfone group, a phosphine oxide group and a phosphonate group, all these radicals being obtained by the addition of oxygen on the sulfur or phosphorus atoms;
    - aromatic or alicyclic heterocyclic radicals comprising at least one heteroatom selected from the group consisting of O, N, S and P;
  - —NO, —CN, —OH, —Cl, —Br, —I, —F;

or two substituents selected from $R_{1n}$ and $R_{2n}$ and/or substituents $R_3$ and $R_4$ and/or substituents $R_5$ and $R_6$ together form a bivalent radical which forms a cycle with the group carrying it, said bivalent radical being selected from the group consisting of linear alkylene radicals having 1 to 18 carbon atoms, benzo biradicals;

- a2) L' represents a bivalent radical selected from the group consisting of linear alkylene radicals having 1 to 18 carbon atoms, substituted or non-substituted phenylene groups, oxaalkylene groups having the formula —R'—(OCH$_2$CH$_2$)$_q$—O—R'— or —R'—OCH(CH$_3$)CH$_2$]$_q$—O—R'— in which R' is a linear alkylene radical having 0 to 18 carbon atoms and $1 \leq q \leq 22$, —O—, —S—, >C=O, siloxane groups —R'—O—[Si(R)$_2$O]$_r$—R'— or —O—[Si(R)$_2$O]$_r$— $1 \leq r \leq 40$ in which R' has the mean given above and R is selected from the group consisting of linear alkyl radicals having 1 to 8 carbon atoms, 2-ethylhexyl, phenyl, or a direct bond between two carbon atoms of two non-condensed aryl groups;

- a3) L represents a bivalent radical selected from the group defined in point a2) above for L'; or L represents a segment made of at least one non-ionic monomer unit or possessing an ionic group which is not sensitive towards the action of actinitic radiation (L in this case representing the average space between the active ionic group);

- a4) p represents the number of recurring units, $2 \leq p \leq 1000$;

- a5) Z represents CH, CR, N, SiR, SiRO$_3$, R being selected from A linear alkyl radical having 1 to 18 carbon atoms, 2-ethylhexyl and phenyl;

- a6) Me represents a transition metal selected from the group of transition elements of column 3 to 12 (lines 3–6) of the Periodic Classification.

4. Polymer or oligomer ionic compound according to claim 1, wherein said perhalogenated cycloaliphatic group contain heteroatoms selected from the group consisting of O and N.

5. Polymer or oligomer ionic compound according to claim 1, wherein said perhalogenated cycloaliphatic group comprises at least one perhaloalkyl chain.

6. Polymer or oligomer ionic compound according to claim 1, wherein said perhalogenated cycloaliphatic group contain hetero atoms selected from the group consisting of O and N, and comprise at least one perhaloalkyl chain.

7. Ionic polymer according to claim 3, wherein $R_{1n}$ represents 1 to 2 groups which are identical or different and are bound to any free carbon atom of the aryl group.

8. Ionic polymer according to claim 3, wherein $R_{2n}$ represents 1 to 2 groups which are identical or different and are bound to any free carbon atom of the aryl group.

9. Ionic polymer according to claim 3, wherein said benzo biradicals carry at least one substituent.

10. Ionic polymer according to claim 3, wherein said R is CH$_3$ or phenyl.

11. Ionic polymer according to claim 9, wherein said at least one substituent is selected from the group consisting of alkyl, oxaalkyl or alkenyl radicals having 1 to 10 carbon atoms, an oxaaikylene group having the formula —R'—(OCH$_2$CH$_2$)$_q$—O—R— or R'—[OCH(CH$_3$)CH$_2$]$_q$—O—R'— in which R' is a linear alkylene radical having 0 to 18 carbon atoms and $1 \leq q \leq 22$.

12. Process for the preparation of an ionic polymer according to claim 2 comprising carrying out a metathesis in water or a water/light alcohol mixture between a salt $(A^+X_1^-)_p$ of the polycation $(A^+)_p$ and a compound $A_1^+X^-$ both being soluble in the reaction mixture, the anion $X_1$ having a hydrophilic character, and the cation $A_1^+$ being selected from alkali and alkali-earth metals.

13. Process according to claim 12 characterized in that the anion $X_1^-$ is a hydroxide, a chloride, a bromide, a hydrogenosulfate, a dihydrogenophosphate or a methylsulfonate.

14. Process for the polymerization or cross-linking of monomers or prepolymers capable of undergoing cationic reaction, wherein said polymerization or cross-linking is carried out in the presence of a photoinitiator constituting a source of acid which catalyzes the reaction, said photoinitiator comprising a polymer or oligomer ionic compound as defined in claim 1.

15. Process according to claim 14 characterized in that the monomers are selected from the group consisting of compounds which have a cyclic ether function, a cyclic thioether fimction or a cyclic amine function, vinyl compounds, vinyl ethers, oxazolines, lactones and lactames.

16. Process according to claim 14 characterized in that the prepolymer is selected from the group consisting of compounds in which epoxy groups are carried by an aliphatic, aromatic or heterocyclic chain.

17. Process according to claim 14 characterized in that it consists in mixing the photoinitiator with at least one monomer or prepolymer which is capable of cationic polymerization, and subjecting the mixture obtained to actinic or β-radiation.

18. Process according to claim 12 characterized in that the reaction mixture is treated with radiation after having been converted into a thin layer.

19. Process according to claim 14 characterized in that the quantity of photoinitiator used amounts to between 0.01 and 15% by weight with respect to the weight of the monomer or prepolymer.

20. Process according to claim 14 characterized in that the photoinitiator is used in the form of a solution in a solvent which is inert towards the polymerization reaction.

21. Process according to claim 20 characterized in that the inert solvent is selected from the group consisting of acetone, methyl-ethyl ketone, acetonitrile, propylene carbonate, γ-butyrolactone, ether-esters of mono-, di-, triethylene or propylene glycols, ether-alcohols of mono-, di-, triethylene or propylene glycols, esters of phthalic acid or citric acid.

22. Process according to claim 14 characterized in that the reaction is carried out in the presence of a solvent or a diluent consisting of a compound which is reactive towards polymerization.

23. Process according to claim 22 characterized in that the reactive compound is selected from the group consisting of vinyl mono- and diethers of mono-, di- tri-tetraethylene or propylene glycols, trivinyl ether trimethylolpropane and divinylether of dimethanol-cyclohexane, N-vinylpyrolidone, 2-propenylether of propylene carbonate.

24. Process according to claim 14 characterized in that a photosensitizer is added to the reaction mixture.

25. Process according to claim 24 characterized in that the photosensitizer is selected from the group consisting of anthracene, diphenyl-9,10-anthracene, perylene, phenothiazine, tetracene, xanthone, thioxanthone, isopropylthioxantone, acetophenone, benzophenone, 1,3,5-triaryl-2-pyrazolines and derivatives thereof.

26. Process according to claim 14 characterized in that the reaction mixture also contains at least one monomer or prepolymer which is capable of free radical polymerization and a compound capable of releasing a free radical polymerization initiator under actinic or β-radiation or under heat.

27. Process for the modification of the solubility properties of a polymer having groups sensitive towards acids, which comprises subjecting said polymer to an actinic or β-radiation, in the presence of a compound according to claim 1.

28. Process according to claim 27 characterized in that the polymer contains units of ester or arylether of tertiary alcohol.

29. Process according to claim 28 characterized in that the polymer is selected from the group consisting of tertiobutyl polyacrylates, tertiobutyl polyitaconates, poly (tertiobutoxycarbonyloxystyrene) and poly (tertiobutoxystyrene).

30. Process according to claim 27 characterized in that it is carried out for the chemical amplification of photoresists.

31. Process according to claim 27 characterized in that it is carried out with a compound having one of the Formulae (III), (VI), (IX), (XV) or (XVIII)

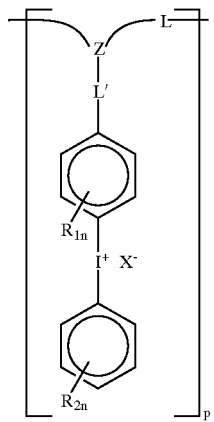

(III)

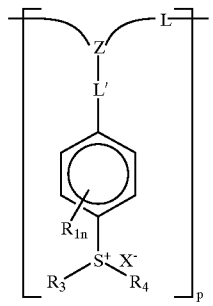

(VI)

(IX) 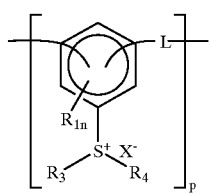
(XV) 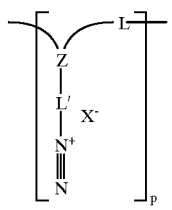
(XVIII) 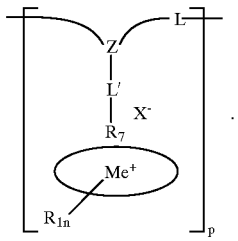
32. Process according to claim 25, wherein said derivations are substituted on the aromatic nuclei by an alkyl, oxa- or azaalkyl radical.
* * * * *